(12) United States Patent
Jang et al.

(10) Patent No.: US 7,232,789 B2
(45) Date of Patent: Jun. 19, 2007

(54) CATALYST FOR PREPARATION OF PENTAFLUOROETHANE AND PREPARATION METHOD THEREOF

(75) Inventors: Hyang Ja Jang, Ulsan (KR); Dae Hyun Kim, Ulsan (KR); Cheol Ho Kim, Ulsan (KR); Young Gu Cho, Ulsan (KR); Jung Eun Lee, Ulsan (KR); Young Su Kim, Ulsan (KR); Yuichi Iikubo, West Lafayette, IN (US)

(73) Assignee: Ulsan Chemical Co., Ltd., Ulsan (KR)

( * ) Notice: Subject to any disclaimer, the term of this patent is extended or adjusted under 35 U.S.C. 154(b) by 0 days.

(21) Appl. No.: 11/288,486

(22) Filed: Nov. 30, 2005

(65) Prior Publication Data

US 2007/0082813 A1    Apr. 12, 2007

(30) Foreign Application Priority Data

Sep. 23, 2005  (KR) ............... 20-2005-0088698

(51) Int. Cl.
    *B01J 23/00* (2006.01)
(52) U.S. Cl. .................................... 502/320; 502/319
(58) Field of Classification Search ............... 502/306, 502/312, 316, 319–321, 340, 338, 353, 355
    See application file for complete search history.

(56) References Cited

U.S. PATENT DOCUMENTS

| | | | | |
|---|---|---|---|---|
| 2,951,816 A | * | 9/1960 | Banks et al. ................ | 502/308 |
| 3,216,954 A | * | 11/1965 | Howk et al. ................. | 502/217 |
| 3,846,340 A | * | 11/1974 | Okuyama et al. ............ | 502/84 |
| 4,550,093 A | * | 10/1985 | Fanelli et al. ............... | 502/107 |
| 5,219,817 A | * | 6/1993 | McDaniel et al. .......... | 502/228 |
| 5,500,400 A | * | 3/1996 | Kim et al. ................... | 502/306 |
| 5,851,948 A | * | 12/1998 | Chuang et al. ............. | 502/314 |
| 6,184,172 B1 | * | 2/2001 | Bonnet et al. .............. | 502/228 |
| 6,433,233 B1 | | 8/2002 | Kanemura et al. | |
| 6,503,865 B1 | * | 1/2003 | Kanemura et al. .......... | 502/224 |
| 6,696,388 B2 | * | 2/2004 | Kourtakis et al. .......... | 502/320 |
| 7,071,371 B2 | * | 7/2006 | Kourtakis et al. .......... | 585/663 |

* cited by examiner

*Primary Examiner*—Cam N. Nguyen
(74) *Attorney, Agent, or Firm*—Egbert Law Offices

(57) ABSTRACT

The method of preparing a chromium oxide catalyst for preparation of pentafluoroethane using a chloroethane compound includes heat treating chromium hydroxide powder at a temperature not higher than 300° C. to obtain chromium oxide powder, heat treating metal hydroxide, at a temperature not higher than 300° C. to obtain metal oxide powder, mixing 85~99.5 wt % of the chromium oxide powder with 0.5~15 wt % of the metal oxide powder to obtain a mixture, forming the mixture into a pellet, calcining the pellet at 200-300° C. using nitrogen gas, and fluorinating the pellet at 300-320° C. using a gas mixture including $N_2$ and HF, and then at 320-380° C. using HF gas. The fluorination catalyst prepared using the method of this invention can be effectively used to prepare pentafluoroethane at a high yield using a chloroethane compound.

4 Claims, 1 Drawing Sheet

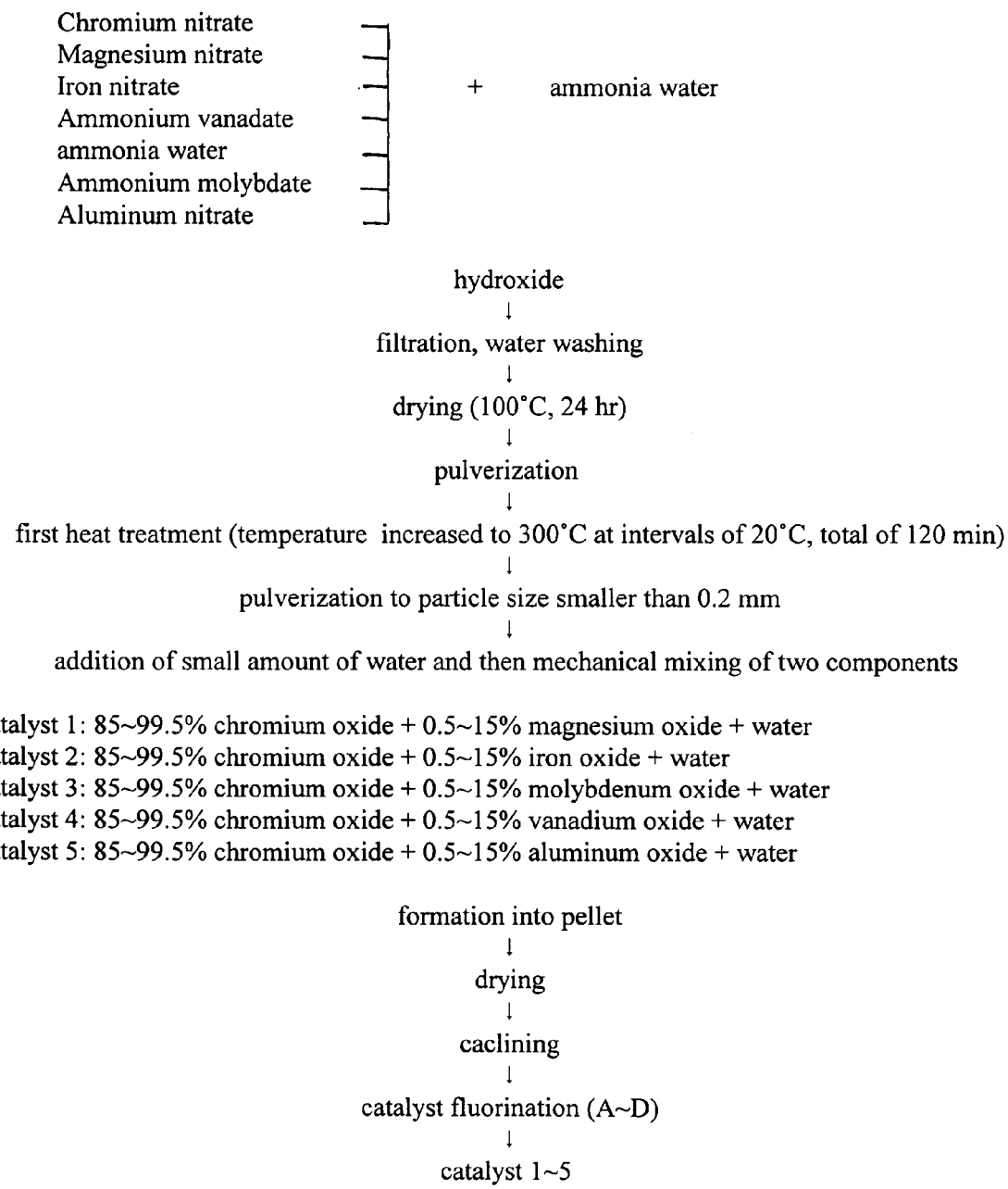

CATALYST FOR PREPARATION OF PENTAFLUOROETHANE AND PREPARATION METHOD THEREOF

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates, generally, to a catalyst for the preparation of pentafluoroethane and a preparation method thereof. More particularly, the present invention relates to a catalyst suitable for use in the preparation of pentafluoroethane ($CF_3CHF_2$, hereinafter, referred to as 'HFC-125') resulting from the reaction of perchloroethane ($C_2Cl_4$, hereinafter, referred to as 'PCE') or 1,1-dichloro-2,2,2-trifluoroethane ($CHCl_2CF_3$, hereinafter, referred to as 'HCFC-123') with HF, and to a method of preparing such a catalyst.

BACKGROUND OF THE INVENTION

Generally, HFC-125 does not contain chlorine in the molecule, and thus has very low impact on global warming and ozone depletion. HFC-125, which is an alternative material of chloro-fluoro-carbon or hydrogen-chloro-fluoro-carbon used as conventional coolants, foaming agents or propellants, is mixed with difluoromethane ($CH_2F_2$, hereinafter, referred to as 'HFC-32') to serve as a material for mixed coolants.

Catalysts for use in the preparation of HFC-125 using chloroethane compounds as raw material are known, almost all of which comprise chromium oxides.

Japanese Patent Laid-open Publication No. Hei. 2-178237 discloses a catalyst for the preparation of HFC-125 using a chloroethane compound, in which the catalyst is exemplified by $Cr_2O_3$—BaO—$Al_2O_3$, $Cr_2O_3$—MgO—$Al_2O_3$, $Cr_2O_3SrO$—$Al_2O_3$, $Cr_2O_3Al_2O_3$, and $Cr_2O_3MgO$.

The $Cr_2O_3Al_2O_3$ catalyst is prepared by dissolving $Cr(NO_3)_3 \cdot 9H_2O$ and water, adding ammonia water with stirring to prepare a precipitate of $Cr(OH)_3$ and $Al(OH)_3$, which is then washed with water, dried and then calcined at 450° C. for 5 hr to obtain $Cr_2O_2Al_2O_3$ powder, forming the powder into a pellet, and then fluorinating the pellet using a gas mixture comprising $N_2$ and HF.

U.S. Pat. No. 6,433,233 discloses $Cr_2O_3/Al_2O_3$, $Cr_2O_3/In_2O_3$, $Cr_2O_3/Ga_2O_3$, $Cr_2O_3/CoO$, $Cr_2O_3/NiO$, and $Cr_2O_3/ZnO$ catalysts.

Of these catalysts, the $Cr_2O_3/Al_2O_3$ catalyst is prepared as follows.

First, ammonia water is added to an aqueous solution of $Cr(NO_3)_3$ to obtain $Cr(OH_3)_3$ precipitate, which is then filtered and dried to obtain $Cr(OH3)3$ solid, which is then pulverized into $Cr(OH_3)_3$ powder. Subsequently, the powder is added to an aqueous solution of $Al(NO_3)_3$, allowed to stand for 12 hr, dried, and added with a small amount of graphite to form a pellet. The pellet thus obtained is calcined for 2 hr using $N_2$ gas and then fluorinated using a gas mixture of $N_2$+HF, thus yielding a desired $Cr_2O_3/Al_2O_3$ catalyst.

In this way, according to the conventional processes of preparing a binary chromium oxide catalyst, such as $Cr_2O_3$—$Al_2O_3$, or a ternary chromium oxide catalyst, $Cr(NO_3)_3$ and $Al(NO_3)_3$ are dissolved in water, after which the obtained solution is coprecipitated using ammonia water to obtain $Cr(OH_3)_3$—$Al(OH)_3$ coprecipitate, which is then calcined to prepare a $Cr_2O_3$—$Al_2O_3$ catalyst (Japanese The use of the chromium oxide catalyst (U.S. Pat. No. 6,433,233), resulting from impregnation of binary or ternary oxides, leads to the following selectivity when using HCFC-123 as a starting material.

| Catalyst | Selectivity (%) | | | |
| --- | --- | --- | --- | --- |
| | HFC-125 | HCFC-124 | HCFC-123 | CFC-115 |
| $Cr_2O_3$—$In_2O_3$ | 67.1 | 14.8 | 17.0 | 0.11 |
| $Cr_2O_3$—$Ga_2O_3$ | 66.9 | 14.9 | 16.9 | 0.17 |
| $Cr_2O_3$—CoO | 67.0 | 22.3 | 8.9 | 0.22 |
| $Cr_2O_3$—NiO | 65.2 | 23.9 | 10.7 | 0.015 |
| $Cr_2O_3$—ZnO | 66.8 | 20.8 | 12.2 | 0.033 |
| $Cr_2O_3$—$Al_2O_3$ | 67.0 | 22.3 | 8.9 | 0.22 |

That is, when the starting material is PCE, the selectivity to HFC-125 is less than 20%. In contrast, the use of HCFC-123 as a starting material results in selectivity to HFC-125 of up to 70%.

Therefore, there is need for the development of a catalyst enabling the conversion of a chloroethane compound and the selectivity to HFC-125 to increase, upon fluorination.

BRIEF SUMMARY OF THE INVENTION

Leading to the present invention, intensive and thorough research on fluorination catalysts, carried out by the present inventors aiming to avoid the problems of insufficient activity of chromium oxide catalysts prepared from binary or ternary oxides through coprecipitation or impregnation processes because the type of heterogeneous metal component mixed with chromium or the catalyst composition ratio is unsuitable for generating or keeping the active site of the catalyst, and also because, even though the metal component is appropriately selected, the chromium catalyst may be insufficiently activated depending on fluorination and preparation processes or the active site thereof may disappear due to sintering, encountered in the related art, resulted in the finding that $Cr(OH)_3$ is heat treated in a temperature range able to maintain the amorphous state of chromium oxide to form $Cr_2O_3$, which is then mechanically mixed with selected heterogeneous metal oxide, Patent Laid-open Publication No. Hei. 2-178237). In addition, $Cr(OH)_3$ powder is impregnated to an aqueous solution of $Al(NO_3)_3$ and then dried to obtain a $Cr(OH)_3/Al(OH)_3$ composition, which is then calcined to prepare a $Cr2O_3/Al_2O_3$ catalyst (U.S. Pat. No. 6,433,233).

The activity of the chromium oxide catalyst is known to be closely connected with the crystalline structure of the catalyst and the valence of Cr.

At the active site of the chromium oxide catalyst disclosed in U.S. Pat. No. 6,433,233, chromium has a valence ranging from +3.5 to +5.0 and is in an amorphous state.

In addition, it is known that the activity of the $Cr_2O_3/Al_2O_3$ catalyst depends on the valence of chromium and that alumina functions as a supporter.

However, the binary or ternary chromium catalysts prepared using impregnation or coprecipitation process suffer because they have low activity and selectivity for a conversion reaction of chloroethane. Thus, the above catalyst is unsuitable for use in commercial preparation processes.

In particular, when HFC-125 is prepared using PCE in the presence of the above catalyst, the conversion and selectivity are low. Further, conventional catalysts do not exhibit sufficient activity upon fluorination.

The use of the chromium oxide catalyst (Japanese Patent Laid-open Publication No. Hei. 2-178237), resulting from coprecipitation of binary or ternary oxides, leads to the following conversion and selectivity when using PCE as a starting material.

| Catalyst | PCE Conversion (%) | Selectivity (%) | | | |
|---|---|---|---|---|---|
| | | HFC-125 | HFC-124 | HFC-123 | HFC-122 |
| $Cr_2O_3$—MgO—$Al_2O_3$ | 90 | 13 | 32 | 35 | 9 |
| $Cr_2O_3$—BaO—$Al_2O_3$ | 82 | 15 | 22 | 37 | 11 |
| $Cr_2O_3$—SrO—$Al_2O_3$ | 80 | 11 | 18 | 40 | 15 |
| $Cr_2O_3$—$Fe_2O_3$ | 75 | 1 | 11 | 27 | 22 |
| $Cr_2O_3$—$Al_2O_3$ | 88 | 12 | 34 | 37 | 11 |
| $Cr_2O_3$—MgO | 93 | 14 | 27 | 42 | 8 | followed by fluorination, thereby increasing the activity of the chromium oxide catalyst.

Accordingly, an object of the present invention is to provide a fluorination catalyst, which enables both the conversion and the selectivity to increase upon preparation of HFC-125 using a chloroethane compound as a raw material.

Another object of the present invention is to provide a method of preparing such a fluorination catalyst.

BRIEF DESCRIPTION OF THE SEVERAL VIEWS OF THE DRAWINGS

FIG. 1 illustrates a schematic view of a process of stepwisely preparing a catalyst, according to the present invention.

DETAILED DESCRIPTION OF THE INVENTION

The present invention pertains to a fluorination catalyst suitable for use in preparation of HFC-125 through fluorination of a chloroethane compound, such as PCE or HCFC-123, and to a preparation method thereof.

The catalyst of the present invention is amorphous and is a chromium oxide-mixed catalyst, comprising chromium oxide, as a main component, and an oxide of a metal selected from among magnesium, iron, molybdenum, vanadium and aluminum.

According to the present invention, the method of preparing the catalyst comprises heat treating chromium hydroxide to be converted into chromium oxide, mixing the chromium oxide thus obtained with oxide of magnesium, iron, molybdenum, vanadium or aluminum, and then fluorinating the mixture, thereby preparing a chromium oxide-mixed catalyst having a specific surface area of 10~30 m$^2$/g while chromium has an average valence ranging from trivalence to pentavalence and is in the amorphous state. This catalyst is advantageous because it can improve the conversion of PCE and HCFC-123 and the selectivity to HFC-125. Upon preparation of the catalyst, since the catalyst activity varies with the fluorination process conditions of the catalyst, optimal fluorination treatment is required.

Below, the catalyst preparation method of the present invention is described. First, an aqueous solution of chromium nitrate (Cr(NO$_3$)$_3$·9H$_2$O) dissolved in water is added with ammonia water (NH$_4$OH) to prepare a blue-gray chromium hydroxide precipitate, which is then filtered. The filtered precipitate is sufficiently washed with hot water and dried. The drying process is preferably conducted at 80~150° C. in air, and more preferably, at about 100° C., for 24-72 hr, and preferably, 72 hr. If the chromium hydroxide precipitate is heat treated in the state of being insufficiently washed and dried, nitrates and ammonium salts remaining therein cause the formation of excess NO$_x$, part of which may remain. The sufficiently dried chromium hydroxide is loaded into an oven or heater, and is then heat treated at 300° C. for 2 hr. At this time, it is preferable that the temperature be gradually increased up to 300° C. at intervals of 20° C. During the temperature-increasing procedure, when the temperature reaches about 200° C., a large amount of yellow NO$_x$ gas is discharged, which circulated to a gas absorption tower for disposal. While impurities (nitrates, ammonium salts, water, etc.) are removed from the catalyst, chromium oxide having the average valence of chromium ranging from trivalence to pentavalence is prepared. In particular, if the residual impurities are not sufficiently removed, NO$_x$ is undesirably generated when fluorinating the catalyst, thus decreasing the strength of the catalyst and producing large amounts of by-products. Therefore, the impurities must be thoroughly removed. After the heat treatment, chromium hydroxide is finely pulverized and mixed with 0.5~5 wt % of another metal oxide obtained through the same procedures and then with a small amount of water, after which the mixture is formed into a pellet. As such, water added in a small amount functions to increase the degree of agglomeration and the strength of the pellet. The pellet is formed to have a cylindrical structure having a diameter of about 12 mm and a height of 12 mm. The catalyst prepared in pellet form is dried.

The catalyst prepared in the form of a pellet is loaded into a reactor, and is then heat treated at 200° C. for 2 hr using nitrogen gas and then at 300° C. for 3 hr using nitrogen gas. Subsequently, the temperature is increased to 320° C., and the nitrogen gas and Hydrogen fluoride gas are simultaneously supplied, whereby the catalyst begins to be fluorinated. When the temperature is gradually increased to 380° C., only the Hydrogen fluoride gas is supplied, without the nitrogen gas, thereby completely fluorinating the catalyst. The higher the temperature and pressure, the faster the fluorination rate. However, the drastic temperature change results in a degraded catalyst. Hence, it is preferable that the temperature be gradually increased. The fluorinated catalyst has a specific surface area of 10~30 m$^2$/g.

In the presence of the catalyst prepared using the method of the present invention, PCE or HCFC-123 is used as a starting material, to synthesize HFC-125. As such, the conversion of the starting material used and the selectivity to HFC-125 vary with the molar ratios of reaction materials, reaction temperatures, contact times, reaction pressures, types of fluorination treatment, etc. The optimal reaction temperature ranges from 350 to 400° C., and the optimal molar ratio of HF and PCE/HCFC-123 ranges from 8/1 to 15/1. The contact time is preferably in the range of 2-20 sec, maximum efficiency being exhibited at 5 sec. The most preferable reaction results are obtained at atmospheric pressure. The selectivity to HFC-125 becomes high in proportion to an increase in reaction temperature and contact time. However, when the reaction pressure is higher than atmospheric pressure, the rate of conversion into HFC-125 is decreased.

A better understanding of the present invention may be obtained in light of the following examples which are set forth to illustrate, but are not to be construed to limit the present invention.

EXAMPLE 1

Fluorinated catalysts 1-5 were prepared according to the processes shown stepwisely in FIG. 1. In FIG. 1, a catalyst 1 was composed of chromium oxide and magnesium oxide, a catalyst 2 of chromium oxide and iron oxide, a catalyst 3 of chromium oxide and molybdenum oxide, a catalyst 4 of chromium oxide and vanadium oxide, and a catalyst 5 of chromium oxide and aluminum oxide. Below, the preparation method of the catalyst composed of chromium oxide and magnesium oxide is described.

To an aqueous solution of 1 kg of chromium (III) nitrate (Cr $(NO_3)_3 \cdot 9H_2O$) dissolved in distilled water, 0.391 kg of ammonia water ($NH_4OH$) were added in droplets, thus obtaining blue-gray chromium hydroxide ($Cr(OH)_3$) precipitate. This precipitate was sufficiently washed with hot distilled water, filtered and dried at about 100° C. for 24 hr, to prepare chromium hydroxide in a solid phase. The chromium hydroxide thus prepared was pulverized into powder using a ball mill or mortar, followed by heat treatment. The heat treatment was conducted while gradually increasing the reaction temperature to 300° C. at intervals of 20° C. and maintaining the temperature at 300° C. for 2 hr. During the heat treatment, in the case where $NO_x$ was generated due to nitrates remaining in chromium hydroxide, it was circulated to an absorption tower for disposal. After the completion of the heat treatment, the resultant material was sufficiently pulverized using a pulverizer. Separately, magnesium nitrate [$Mg(NO_3)_2 \cdot 6H_2O$] was treated in the same manner as in the above procedures to obtain magnesium hydroxide, which was then heat treated as mentioned above, thus obtaining magnesium oxide (MgO) powder.

98 wt % of chromium oxide was mixed with 2 wt % of magnesium oxide powder, after which water was added in an amount sufficient to mix the two oxides, to obtain a reaction mixture, which was then formed into a pellet using a pelletizer. The pellet was in a cylindrical shape having a diameter of about 12 mm and a height of 12 mm, and was then dried at 100° C. for about 48 hr before being loaded into a reactor. Into a 1 inch and 500 mm sized cylindrical reactor, about 150 g of the catalyst thus obtained was loaded and then calcined at 200° C. for 2 hr and then at 300° C. for 3 hr in the presence of nitrogen. Subsequently, the temperature was increased to 320° C. and hydrofluoric acid gas and nitrogen gas were simultaneously supplied to initiate the fluorination of the catalyst. For about 30 min, the catalyst was reacted with the gas mixture comprising Hydrogen fluoride gas and nitrogen gas, and then with only the Hydrogen fluoride gas, without the nitrogen gas. The temperature was stepwisely increased to 380° C., and the hydrofluoric acid gas was continuously supplied, thereby completely fluorinating the catalyst. After the completion of the fluorination, the nitrogen gas was supplied to discharge non-reacted Hydrogen fluoride gas and gaseous impurities, thereby preparing a desired catalyst 1. The catalyst thus prepared was confirmed to be amorphous using an x-ray diffractometer. In addition, the catalyst had a specific surface area ranging from 10 to 30 $m^2/g$, measured using a surface area analyzer (BET).

EXAMPLE 2

<Preparation of Catalyst 2 (Chromium Oxide-Iron Oxide Catalyst)>

A catalyst 2 was prepared in the same manner as in Example 1, with the exception that iron nitrate [Fe$(NO_3)_2 \cdot 6H_2O$] was used, instead of magnesium nitrate.

EXAMPLE 3

<Preparation of Catalyst 3 (Chromium Oxide-Molybdenum Oxide) Catalyst>

A catalyst 3 was prepared in the same manner as in Example 1, with the exception that ammonium molybdate [$(NH_4)_6Mo_7O_{24}$] was used, instead of magnesium nitrate.

EXAMPLE 4

<Preparation of Catalyst 4 (Chromium Oxide-Vanadium Oxide) Catalyst>

A catalyst 4 was prepared in the same manner as in Example 1, with the exception that ammonium vanadate ($NH_4VO_3$) was used, instead of magnesium nitrate.

EXAMPLE 5

<Preparation of Catalyst 5 (Chromium Oxide-Aluminum Oxide) Catalyst>

A catalyst 5 was prepared in the same manner as in Example 1, with the exception that aluminum nitrate [Al$(NO_3)_3 \cdot 9H_2O$] was used, instead of magnesium nitrate.

The crystalline structure and specific surface area of each of the catalysts prepared in Examples 2-4 were confirmed to be amorphous and 10~30 $m^2/g$, using an X-ray diffractometer and a BET, respectively.

Experimental Example

<Fluorination of PCE>

PCE was fluorinated using HF gas in the presence of each of the catalysts 1-5 obtained in Examples 1-5 under the following reaction conditions.

Reaction Conditions:

Catalyst Amount: 150 g

Reactor: 25.4 mm (ID), SUS 316L

Reactive Gas: PCE (6.9 g/min), HF (300 sccm)

Contact Time: 10 sec

Reaction Temperature: 350° C., 300° C.

Reaction Pressure: atmospheric pressure

After PCE was fluorinated under the above reaction conditions, the resultant gas was passed through an aqueous potassium hydroxide solution out of the reactor, and then the reaction product gas was analyzed using gas chromatography. The results at reaction temperature of 300° C. are given in Table 1 below, and those at the reaction temperature of 350° C. in Table 2 below.

TABLE 1

| | Catalyst | | | | |
|---|---|---|---|---|---|
| | Catalyst 1 | Catalyst 2 | Catalyst 3 | Catalyst 4 | Catalyst 5 |
| Reaction Temp. | 350 | 350 | 350 | 350 | 350 |
| PCE Conversion | 98.7 | 98 | 96.1 | 96.3 | 94.9 |
| Composition of Organics (mol %) | | | | | |
| HFC-125 | 66.5 | 64.9 | 62 | 62.3 | 61 |
| HCFC-124 | 15.5 | 14.5 | 13 | 13.4 | 11 |
| HCFC-123 | 2 | 2.5 | 0.5 | 1 | 0.8 |
| HCFC-122 | 0.5 | 0.3 | 1.6 | 2.0 | 1.3 |
| CFC-115 | 4.6 | 4.6 | 5.6 | 5.2 | 5.6 |
| CFC-114 | 3 | 3.2 | 4.9 | 3.7 | 5.2 |
| CFC-113 | 0.3 | 0.3 | 0.7 | 0.7 | 2.3 |
| HCFC-133 | 6.2 | 8.3 | 9.3 | 9.3 | 9.7 |
| R-1111 | 1.4 | 1.4 | 2.4 | 2.4 | 3.1 |

TABLE 2

| | Catalyst | | | | |
|---|---|---|---|---|---|
| | Catalyst 1 | Catalyst 2 | Catalyst 3 | Catalyst 4 | Catalyst 5 |
| Reaction Temp. | 300 | 300 | 300 | 300 | 300 |
| PCE Conversion | 84 | 83.7 | 81.5 | 81.3 | 80.1 |
| Composition of Organics (mol %) | | | | | |
| HFC-125 | 43.9 | 43.6 | 41.9 | 41.9 | 40.2 |
| HCFC-124 | 32.7 | 33.7 | 35.7 | 35.5 | 37 |
| HCFC-123 | 10.6 | 10 | 11 | 11.1 | 10.4 |
| HCFC-122 | 0.9 | 0.9 | 0.9 | 0.8 | 1.3 |
| CFC-115 | 0.9 | 1 | 1 | 1.2 | 1 |
| CFC-114 | 3.7 | 3.7 | 3.0 | 3.1 | 3.9 |
| CFC-113 | 0.8 | 0.7 | 0.7 | 0.7 | 0.7 |
| HCFC-133 | 4.5 | 4.2 | 3.7 | 3.7 | 3.1 |
| R-1111 | 2 | 2.2 | 1.9 | 2 | 2.4 |

When HFC-125 was synthesized using PCE as a starting material in the presence of the catalyst prepared as above, the conversion of PCE was 94.9% or more at a reaction temperature of 350° C., and the conversion of PCE was 80.1% or more at a reaction temperature of 300° C. The selectivity to HFC-125 was 61% and 40.2% or more at 350° C. and 300° C., respectively. From these results, it can be seen that the use of PCE as a starting material in the presence of the catalyst of the present invention results in a selectivity similar to that of the use of HCFC-123 as a starting material in the presence of a conventional chromium oxide-mixed catalyst. However, in consideration of the fact that the synthesis of HFC-125 using PCE is more difficult than that using HCFC-123, the activity of the catalyst of the present invention can be regarded to be very high. The catalyst of the present invention, comprising chromium oxide and only 2 wt % of oxide of Mg, Fe, Mo, V or Al to have high catalyst activity, can improve the reaction activity and selectivity to HFC-125. In addition, even though metal oxide is added in a small amount of 0.5 wt % to chromium oxide, the selectivity can be increased. However, the addition of metal oxide exceeding 15 wt % decrease the activity and selectivity, on the contrary. Thus, the amount of metal oxide is preferably determined in the range of 0.5~15 wt % relative to the amount of chromium oxide. Moreover, the catalyst of the present invention is advantageous because it has an induction period, able to cause uniform yield and selectivity upon an initial reaction, much shorter than a pure chromium oxide catalyst, under the same reaction conditions. The catalyst activity of metal oxide used increases according to the sequence of Mg>Fe>V>Mo>Al.

<Catalyst Activity Test by Types of Fluorination Treatment>

To investigate the reaction activity of the catalyst varying with types of fluorination treatment, the fluorination of HF gas and HCFC-123 was conducted using the catalyst 2 under the following reaction conditions.

Reaction Conditions:
Catalyst Used: catalyst 2
Contact Time: 5 sec
Reactor: 25.4 mm (ID), SUS 316L
Reactive Gas: HCFC-123 (12.5 g/min), HF (590 sccm)
Reaction Temperature: 350° C.
Reaction Pressure: atmospheric pressure

| Types of Fluorination Treatment of Catalyst |
|---|
| Fluorination A |
| Burning (air (90 ml/min), 200° C., 1 hr) ↓ |
| Burning (air (90 ml/min), 300° C., 1 hr) ↓ |
| Burning (air (90 ml/min), 400° C., 3 hr) ↓ |
| Supply of Hydrogen fluoride (HF) (HF(610 seem), 400° C., 15 hr) ↓ |
| Nitrogen Purging ↓ |
| Reaction |
| Fluorination B |
| Burning (nitrogen (10 ml/min), 200° C., 2 hr) ↓ |
| Burning (nitrogen (20 ml/min), 300° C., 3 hr) ↓ |
| Supply of Nitrogen (10 ml/min) + HF(500 sccm) (300° C., 20 min) ↓ |
| Supply of Nitrogen (10 ml/min) + HF(500 sccm) (320° C., 10 min) ↓ |
| Supply of HF(500 sccm) (320° C., 10 min) ↓ |
| Supply of HF(500 sccm) (340° C., 10 min) ↓ |
| Supply of HF(500 sccm) (360° C., 20 min) ↓ |
| Supply of HF(610 sccm) (360° C., 90 min) ↓ |
| Supply of HF (610 sccm) (380° C., 60 min) ↓ |
| Nitrogen Purging (380° C., 90 min) ↓ |
| Reaction |
| Fluorination C |
| Burning (nitrogen (10 ml/min), 200° C., 2 hr) ↓ |
| Burning (nitrogen (20 ml/min), 300° C., 3 hr) ↓ |
| Supply of Nitrogen (10 ml/min) + HF(500 sccm) (300° C., 20 min) ↓ |
| Supply of Nitrogen (10 ml/min) + HF(500 sccm) (320° C., 10 min) ↓ |
| Supply of HF(500 sccm) (320° C., 10 min) |

-continued

Types of Fluorination Treatment of Catalyst

↓
Supply of HF(500 sccm) (340° C., 10 min)
↓
Supply of HF(500 sccm) (360° C., 20 min)
↓
Supply of HF(610 sccm) (360° C., 90 min)
↓
Supply of HF (610 sccm) (380° C., 180 min)
↓
Nitrogen Purging (380° C., 90 min)
↓
Reaction
Fluorination D Burning(nitrogen (10 ml/min), 200° C., 2 hr)
↓
Burning (nitrogen (20 ml/min), 300° C., 3 hr)
↓
Supply of Nitrogen (10 ml/min) +
HF(500 sccm) (300° C., 20 min)
↓
Nitrogen (10 ml/min) + HF(500 sccm)
(320° C., 10 min)
↓
Supply of HF(500 sccm) (320° C., 10 min)
↓
Supply of HF(500 sccm) (340° C., 10 min)
↓
Supply of HF(500 sccm) (360° C., 20 min)
↓
Supply of HF(610 sccm) (360° C., 300 min)
↓
Supply of HF (610 sccm) (380° C., 60 min)
↓
Nitrogen Purging (400° C., 90 min)
↓
Reaction The results are given in table 3 below.

TABLE 3

|  | Type of Fluorination Treatment | | | |
|---|---|---|---|---|
|  | A | B | C | D |
| HCFC-123 Conversion | 71.8 | 96.5 | 95.7 | 96 |
| Composition of Organics (mol %) | | | | |
| HFC-125 | 19.9 | 86 | 78.5 | 80 |
| HCFC-124 | 77.3 | 9.5 | 8.6 | 8.9 |
| CFC-115 | 0.18 | 1.7 | 5.6 | 4.5 |
| CFC-114 | 0.3 | 0.5 | 0.5 | 0.7 |
| HCFC-133 | 2.4 | 2.9 | 6.6 | 6.2 |

As is apparent from the above results, the types affect of fluorination treatment of the catalyst greatly the catalyst activity and selectivity. In the A type of fluorination treatment, since the fluorination is conducted at a high temperature, not lower than 400° C., for a long period of time, chromium oxide is deformed into a crystalline structure of $Cr_2O_3$ resulting in drastically decreased catalyst activity and selectivity. On the other hand, in the B, C and D types of fluorination treatment, the activity of the catalyst fluorinated at a temperature less than 400° C. for a short period of time is noted to be excellent. Since the catalyst, obtaining through fluorination at 380° C. for 60~180 min, is in an amorphous state, the conversion of PCE or HCFC-123 and the selectivity to HFC-125 can be seen to be high. In this way, it is noted that the activity of the catalyst is affected by the treatment time, as well as the treatment temperature, upon fluorination. That is, when the fluorination of the pellet using HF gas is conducted at 380° C. for a time period not exceeding 3 hr, the catalyst activity can be confirmed to be the maximum.

In addition, in order to investigate the effect of activity of the catalyst depending on the reaction temperature, the reaction was conducted using the catalyst 2 under the following reaction conditions.

Reaction Conditions:
Catalyst Used: catalyst 2
Contact Time: 10 sec
Reactor: 25.4 mm (10), SUS 316L
Reactive Gas: PCE (6.9 g/min), HF (300 sccm)
Reaction Temperature: 300° C., 330° C., 350° C.
Reaction Pressure: atmospheric pressure The results are given in Table 4 below.

TABLE 4

|  | Type of Fluorination Treatment | | |
|---|---|---|---|
|  | B | B | B |
| Reaction Temp. | 300° C. | 330° C. | 350° C. |
| PCE Conversion | 83.7 | 90.3 | 98 |
| HFC-125 | 43.6 | 53 | 64.9 |
| HCFC-124 | 33.7 | 12 | 14.5 |
| HCFC-123 | 10 | 15 | 2.5 |
| HCFC-122 | 0.9 | 0.6 | 0.3 |
| CFC-115 | 1 | 2.4 | 4.6 |
| CFC-114 | 3.7 | 4.5 | 3.2 |
| CFC-113 | 0.7 | 0.3 | 0.3 |
| HCFC-133 | 4.2 | 2.2 | 6.8 |
| F-1111 | 2.6 | 8.3 | 1.4 |

As is apparent from Table 4, the higher the reaction temperature, the higher the selectivity to HFC-125 and the conversion of PCE. As described above, the present invention provides a catalyst for preparation of HFC-125 and a preparation method thereof. The fluorination catalyst prepared using the method of the present invention can be effectively used to prepare HFC-125 at a high yield using a chloroethane compound as a raw material.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

We claim:

1. A method of preparing a chromium oxide catalyst for preparation of pentafluoroethane from a chloroethane compound, said method comprising the steps of:

heat treating a chromium hydroxide powder at a temperature not higher than 300° C. to obtain chromium oxide powder;

heat treating a metal hydroxide at a temperature not higher than 300° C. to obtain metal oxide powder, said metal hydroxide being selected from a group consisting of magnesium hydroxide, iron hydroxide, molybdenum hydroxide, vanadium hydroxide and aluminum hydroxide;

mixing 85% to 99.5% by weight of said chromium oxide powder with 0.5% to 15% by weight of the metal oxide powder so as to obtain a mixture;

forming said mixture into a pellet;
burning said pellet at 200° C. to 300° C. with nitrogen gas; and
fluorinating the burned pellet at 300° C. to 320° C. with a gas mixture containing $N_2$ and HF and then at 320° C. to 380° C. with HF gas.

2. The method of claim 1, the chloroethane compound being perchloroethane or 1,1-dichloro-2,2,2-trifluoroethane.

3. The method of claim 1, wherein the step of heat treating a metal hydroxide comprises heat treating the metal hydroxide at a temperature of 300° C. for a time period of 2 hours, said heat treating being carried out under atmospheric conditions.

4. The method of claim 1, wherein the step of fluorinating the burned pellet comprises fluorinating the burned pellet with HF gas at a temperature of 380° C. for a time period of no more than 3 hours.

* * * * *